(12) United States Patent
Moir

(10) Patent No.: US 7,462,164 B2
(45) Date of Patent: Dec. 9, 2008

(54) DEVICE FOR PREPARING A MEDICINAL LIQUID AND METHOD FOR PRESERVING A SOLUTION OF MEDICAMENT FOR INJECTION

(75) Inventor: Andrew Moir, Le Vaud (CH)

(73) Assignee: Ares Trading S.A., Aubonne (CH)

( * ) Notice: Subject to any disclaimer, the term of this patent is extended or adjusted under 35 U.S.C. 154(b) by 44 days.

(21) Appl. No.: 10/972,277

(22) Filed: Oct. 22, 2004

(65) Prior Publication Data
US 2005/0113747 A1 May 26, 2005

Related U.S. Application Data

(63) Continuation of application No. PCT/CH03/00167, filed on Mar. 13, 2003.

(51) Int. Cl.
*A61M 37/00* (2006.01)
(52) U.S. Cl. ............... 604/82; 604/86; 604/414
(58) Field of Classification Search ............ 604/82–88, 604/411–415
See application file for complete search history.

(56) References Cited

U.S. PATENT DOCUMENTS

| | | | |
|---|---|---|---|
| 3,914,419 A | 10/1975 | Haeger | |
| 4,338,980 A | 7/1982 | Schwebel | |
| 5,569,191 A * | 10/1996 | Meyer | 604/82 |
| 5,603,695 A | 2/1997 | Erickson | |
| 5,649,912 A | 7/1997 | Peterson | |
| 5,827,262 A * | 10/1998 | Neftel et al. | 604/414 |
| 5,894,015 A | 4/1999 | Rechtin | |
| 6,162,199 A | 12/2000 | Geringer | |
| 6,312,412 B1 | 11/2001 | Saied | |
| 6,364,866 B1 | 4/2002 | Furr | |
| 2003/0055376 A1 * | 3/2003 | Delay | 604/82 |

FOREIGN PATENT DOCUMENTS

| | | |
|---|---|---|
| FR | 2775603 | 9/1999 |
| WO | WO 97/46203 | 12/1997 |
| WO | WO 01/30425 | 5/2001 |

* cited by examiner

*Primary Examiner*—Kevin C Sirmons
*Assistant Examiner*—Phillip Gray
(74) *Attorney, Agent, or Firm*—Sturm & Fix LLP

(57) ABSTRACT

This device comprises means for supporting a first and a second chamber, means for allowing these chambers to communicate with each other, and a movable member for applying a suitable force to reduce the volume of the first chamber. The means for supporting the first and second chambers comprise two tubular bodies, each open at one end, the dimensions of these openings being such as to allow these tubular bodies to be brought together and slid one into the other, a double-ended needle, with associated guide means, being interposed between the said chambers in such a way that when the said tubular bodies are slid towards each other, the respective ends of the said needle pass into the chambers and the volume of the chamber is reduced.

21 Claims, 2 Drawing Sheets

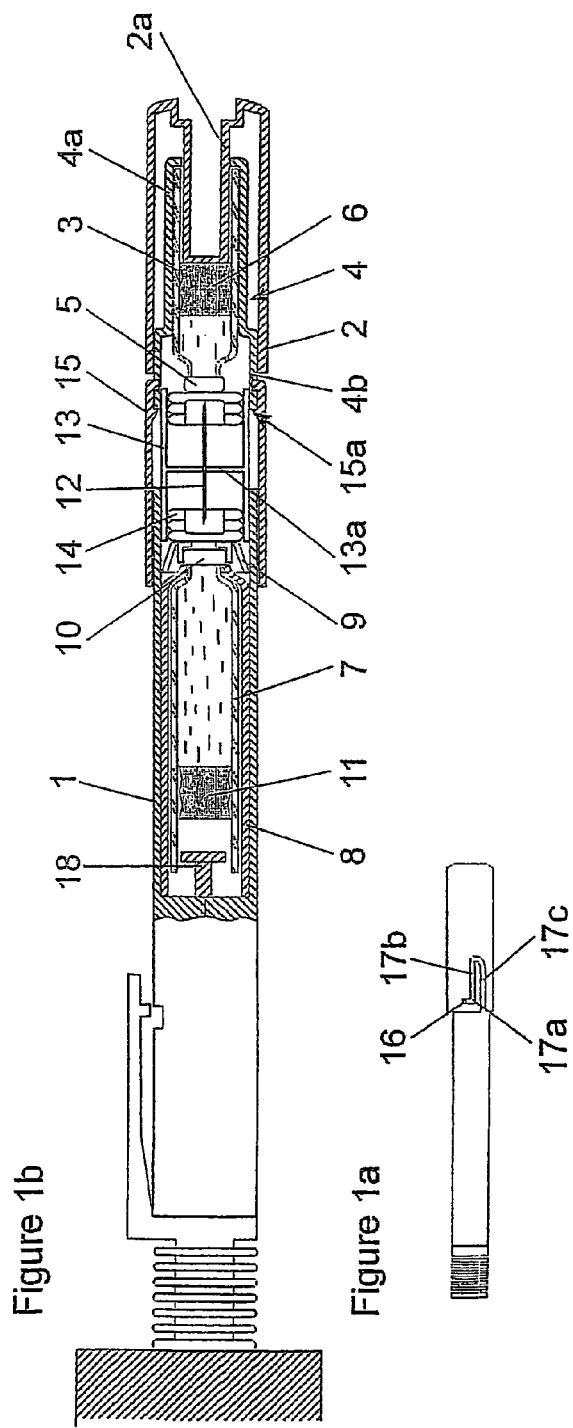
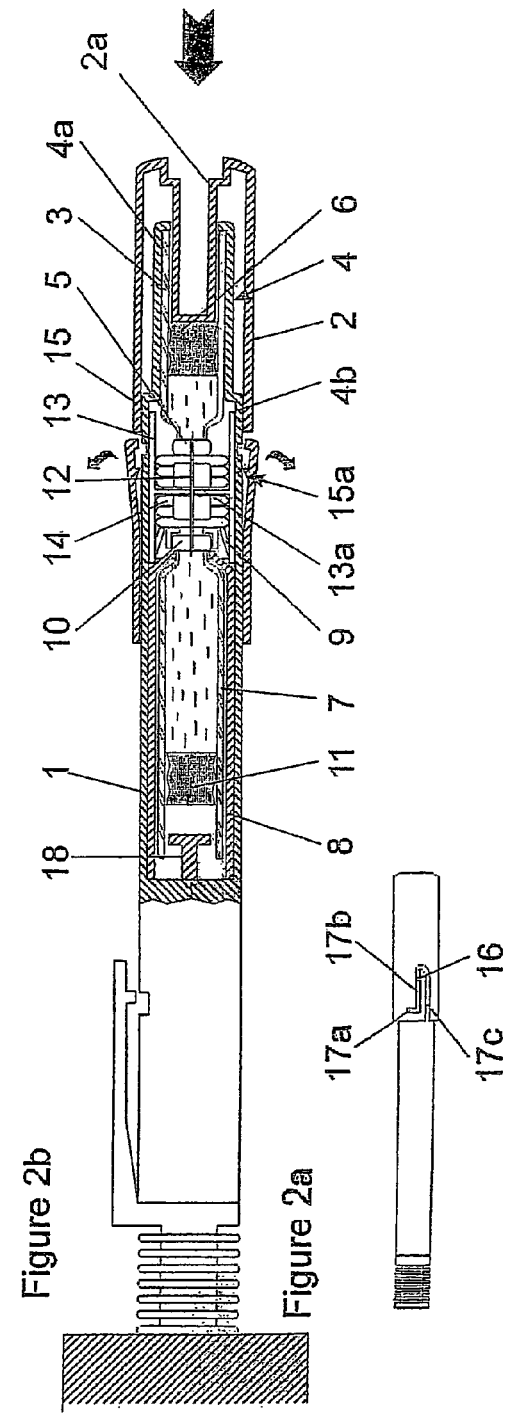
Figure 1b  Figure 1a  Figure 2b  Figure 2a

DEVICE FOR PREPARING A MEDICINAL LIQUID AND METHOD FOR PRESERVING A SOLUTION OF MEDICAMENT FOR INJECTION

CROSS REFERENCE TO RELATED APPLICATIONS

This application is a continuation of PCT/CH2003/000167 filed Mar. 13, 2003, claiming priority of European Application No. 02405338.1 filed Apr. 24, 2002, which is included in its entirety by reference made hereto.

BACKGROUND OF THE INVENTION

1. Field of the Invention

The present invention relates to a device for preparing a medicinal liquid by combining a first liquid substance contained in a first variable-volume chamber and a second substance contained in a second chamber, this device comprising means for supporting the first and second chambers, means for allowing these chambers to communicate with each other and a movable member for applying a suitable force to reduce the volume of the said first chamber in order to transfer the liquid from the first chamber to the second chamber. It also relates to a unit for preparing and injecting a medicinal liquid and to a method for preserving a solution of medicament for injection.

2. Description of Related Art

Several devices of this kind have already been proposed for the purpose of mixing two substances, particularly for preparing a medicinal liquid with a short storage life. Such devices can be used by nursing staff or by the patient him or herself to prepare the liquid by mixing the two substances at the desired time.

Such a device was proposed in WO 97/46203, more particularly for reconstituting a medicinal liquid by diluting or suspending a solid substance contained in a vial with the aid of a liquid contained in a chamber and introduced into the vial through a needle, the liquid being pushed by sliding a plunger along the inside of the chamber of liquid, after which the diluted substance is returned to the chamber.

Another proposal, made in U.S. Pat. No. 4,338,980, was for a device for filling an injector from the front from a vial containing the medicine, the bottom of which comprises a plunger which is pushed towards the dispensing opening of the injector. Under pressure, the liquid enters the injector through this orifice and the plunger of the injector moves back as the liquid is transferred from the vial into the injector.

Besides the cases cited above, there are medicines that contain injectable proteins to which a bactericidal liquid must be added. However, this bactericidal liquid must not be placed in contact with the proteins for any length of time before the medicine is used, as for example at the manufacturing stage, which is why the medicinal liquid is produced and packaged without the bactericidal liquid, which must be added only a short time before the medicinal liquid is used.

Many injectable medicaments, such as proteins, must be administered repeatedly over a given prolonged period. Such medicaments are often formulated in solutions contained in vials which contain sufficient material for multiple injections (for example, for one to two weeks). These vials can be filled and sealed under sterile conditions, in such a manner that the medicament solution has a considerable shelf life (usually at least 12 months, and sometimes as long as 24 months). However, once the seal of the vial has been compromised (e.g. at the time of first use), the shelf life of such vials is very short, due to bacterial contamination and growth. To attempt to overcome this problem, a bacteriostat has been added to the medicament solution at the time the vial is filled and sealed. This suffers the considerable drawback that many bacteriostats interact negatively with medicaments in solution over prolonged periods, with the result that the medicament may be degraded or precipitated due to interaction with the bacteriostat while the vial sits on the shelf.

The disadvantage of existing devices arises from the fact that they necessitate relatively complicated handling. Furthermore, the amount of liquid transferred depends on the displacement of the plunger, and there is no guarantee that the required amplitude of this displacement has actually been complied with, given that the displacement is indicated by marks which there is no compulsion on the user to observe. As a result there is no certainty as to the amount of liquid transferred because such amount depends on whether or not the required displacement is complied with, which can obviously have serious consequences on the patient.

BRIEF SUMMARY OF THE INVENTION

The object of the present invention is to solve, at least in part, the abovementioned drawbacks.

For this purpose, the subject of this invention is a device for preparing a medicinal liquid by combining a first liquid substance contained in a first variable-volume chamber and a second substance contained in a second chamber, according to claim 1. It also relates to a unit for preparing and injecting a medicinal liquid.

In a further aspect, the invention provides a method for preserving a solution of medicament for injection, the method comprising:

to a quantity of the solution of medicament sufficient for a predetermined multi-dose injection period, adding a bacteriostatic agent at the time of first use;

wherein the quantity of the solution and the bacteriostatic agent are such that the medicament is maintained substantially sterile and suitable for injection throughout the predetermined multi-dose injection period.

The method of the invention overcomes the problems associated with formulating the medicament for long storage in solution with a bacteriostatic agent. The medicament can be formulated in a container, such as a cartridge, vial or ampoule, under sterile conditions, sealed with minimal preservative agent or even without any preservative agent, and stored for long periods, prior to use. The bacteriostatic agent is then added immediately before, during or immediately after the first use, preferably by the patient. The bacteriostatic agent is preferably added the first time the seal of the cartridge, vial or ampoule is compromised, and more preferably, it is the addition of the bacteriostatic agent that constitutes the first breach of the seal of the cartridge, vial or ampoule.

The bacteriostatic agent will keep the solution of medicament essentially free of bacterial contamination, even though the seal of the cartridge, vial or ampoule containing the medicament has been compromised. Because the bacteriostatic agent is added immediately prior to, during or immediately after the first use, the time period over which it may interact detrimentally with the medicament is minimised. The multi-dose injection period will be finished within a time period that is too short for any substantial reaction between the medicament and the bacteriostatic agent.

The method of the invention is suited for use with solutions comprising any medicament that must be repeatedly administered. Preferred examples of medicament include injectable biologicals, such as vaccines, carbohydrates or proteins.

Examples of injectable carbohydrates include for example, heparin.

Examples of injectable proteins include, for example, protein hormones (e.g. insulin, growth hormone, FSH, LH, CG, GnRH and GnRH agonists and antagonists), cytokines (e.g. α-, β- and γ-interferon), binding proteins and antibodies (e.g. IL-18 binding protein, remicaide, enbrel), growth factors (e.g. epidermal growth factor, erythropoietin, basic fibroblast growth factor, granulocyte colony stimulating factor, granulocyte macrophage colony stimulating factor, insulin-like growth factor- and -2, interleukins, leukaemia inhibitory factor, macrophage colony stimulating factor, oncostatin, thrombopoietin, transforming growth factor, tumour necrosis factor, vascular endothelial growth factor), blood factors (e.g. factor VIII).

Also included are small molecule medicaments that may be administered repeatedly, such as thyroxine, epinephrine, and morphine.

The quantity of the solution is preferably an amount sufficient for 30 or fewer injections, more preferably 28 or fewer injections, or 2 to 14 injections, particularly preferably 7 to 14 injections. The solution is preferably an amount sufficient for a multi-dose injection period of 30 days or less, more preferably from 2 to 28 days, particularly preferably for 2 to 14 or 7 to 14 days. The solution is preferably sealed in an aseptic vial, which can be stored prior to the first use for prolonged periods (usually from at or about 1 year to at or about 2 years). The medicament vial may contain additional agents and excipients, such as are commonly used in the art. For example, some proteins may be formulated with a bulking agent (e.g. sucrose, lactose, mannitol, glucose, etc.), a buffering agent (phosphate, citrate, acetate, etc.), and stabilising agents (antioxidants, surfactants, HSA).

The bacteriostatic agent may be any agent that is compatible with the medicament over the given period, and which is capable of maintaining the medicament in substantially sterile, intact and active form, and which can be injected without adverse effects. Examples of bacteriostatic agents include benzyl alcohol, borate, boric acid, meta-cresol, phenol, metabisulphite salts, sulphite salts, bisulphite salts, chlorobutanol, methylparaben, propylparaben, butylparaben, thimerosal, phenylmercuric nitrate, benzalkonium chloride, benzethonium chloride, sodium formaldehyde sulphoxylate, ethyl gallate, acetone sodium metabisulphite, phosphoric acid, thiodipropionic acid, acetonic dicarboxylic acid.

In a particularly preferred embodiment, the medicament is an injectable protein. The medicament is supplied to the user sealed in a cartridge, vial or ampoule, as a solution of at or about 0.5 ml to at or about 10 ml. The cartridge, vial or ampoule is filled and sealed by the manufacturer under sterile conditions, and can be stored for prolonged periods. Immediately prior to the first use (i.e. the first time the seal of the cartridge is compromised), the user adds a solution of bacteriostatic agent, preferably benzyl alcohol, to the solution containing the medicament. Benzyl alcohol is added in an amount sufficient to bring the final concentration of benzyl alcohol to at or about 0.5% to 2% (wt/wt), preferably at or about 0.8% to 1.5%, more preferably to at or about 1%. Periodic injections can then be made, using the same cartridge, vial or ampoule. For example, if the medicament is growth hormone, daily injections may be made for from at or about 2 or 3 days to at or about 14 days, at which point the cartridge which contained the medicament may be discarded.

Less preferably, the patient may make a first injection of the medicament without adding any preservative agent, and then add the preservative agent to the remainder of the contents of the vial containing the medicament. This is less preferred because the first injection will contain a different protein concentration than subsequent injections.

If m-cresol is used as the preservative agent, it is preferably added to the solution of the medicament in an amount sufficient to bring the final concentration to at or about 1 to 5 mg/ml m-cresol, more preferably at or about 3 mg/ml m-cresol. If phenol is used as the preservative agent, it is preferably added to the solution of the medicament in an amount sufficient to bring the final concentration to at or about 1 to 5 mg/ml phenol, more preferably at or about 3 mg/ml phenol.

The addition of the bacteriostatic agent to the medicament solution may be accomplished, for example, by injecting a solution of the bacteriostatic agent into the cartridge, vial or ampoule containing the solution of the medicament, with a conventional syringe. The medicament may be supplied to the user in the form of a kit, comprising one or more multi-dose vials of medicament and one or more vials of preservative agent. Alternatively, and more preferably, the addition of the preservative agent to the medicament is carried out using a device as disclosed herein, thus avoiding the use of un-protected needles, and ensuring that the addition of the preservative agent is carried out correctly.

By means of the device and the preparation unit to which the present invention relates, the person preparing the medicinal liquid, who may be a careworker or the patient him or herself, is no longer required to carry out more or less complex, even difficult procedures. All he or she holds is an instrument resembling a simple pen. The only operation he or she has to carry out is to push the two parts of the device together. When the required displacement has been accomplished, the two sliding parts can be separated from each other, the first chamber and the means for enabling communication between these chambers can be removed and the medicinal liquid in the second chamber can be used. The concentration of this liquid is therefore completely independent of the person carrying out the preparation.

Since all component parts are advantageously preassembled and cannot be separated until the required volume of liquid has been transferred from the first chamber to the second, this constitutes a guarantee that the device or unit cannot be tampered with, unlike devices which have to be assembled by the user him or herself. This represents a guarantee as to the aseptic condition and the nature of the liquids mixed.

Other features and advantages will become apparent in the course of the following description, which is given with the help of the accompanying drawings showing schematically and by way of example one embodiment of the device and of the unit forming the subject of the present invention.

BRIEF DESCRIPTION OF THE DRAWINGS

FIG. 1a is a side view of this embodiment with its component parts in the preassembled starting position;

FIG. 1b is an axial section through FIG. 1a on a larger scale;

FIG. 2a is a view similar to FIG. 1a, showing the device at the beginning of the process of transferring liquid from the first chamber to the second;

FIG. 2b is an axial section through FIG. 2a on a larger scale;

Figure 3B:
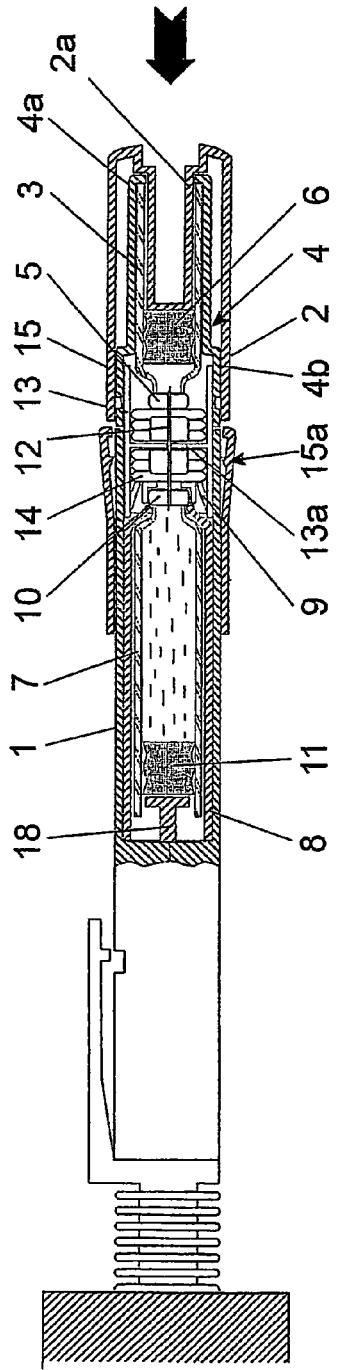
FIG. 3b is an axial section through FIG. 3a on a larger scale.

The device according to the present invention comprises two tubular parts 1, 2 that slide one inside the other via their respective open ends. A first chamber, consisting in this example of a vial 3 filled with liquid, such as a bactericidal liquid, is held in position inside one 2 of the tubular parts by an internal tubular support 4 which comprises two sections of different diameters, a smaller-diameter section 4a in which the vial 3 is held, and a larger-diameter section 4b that corresponds to the inside diameter of the tubular part 2.

The forward end of the vial 3 is closed, in a known manner, by an elastomeric film (not shown) sealed to this end by an annular metal cap 5, leaving the centre of the film exposed. The body of this vial 3 is tubular and its rear end is open. A plunger 6 is engaged in the tubular body of this vial 3, thereby defining a variable volume inside the vial 3. This plunger 6 rests against a cylindrical pusher 2a projecting from the end of the tubular part 2.

A second tubular chamber, consisting in this example of a cartridge 7 prefilled with a liquid, such as a protein-containing liquid, is held in position inside the other tubular chamber 1 by an internal tubular support 8 and is retained by a lock ring 9.

The end of this cartridge 7 facing towards the vial 3 is also closed in a known manner by an elastomeric film (not shown) which is held in position in a sealed manner by an annular cap 10, leaving the centre of the film exposed. The internal tubular support 8 rests against the back of the annular cap 10, thus preventing the cartridge from moving backwards inside the tubular part 1. The other end of this cartridge 7 is closed by a plunger 11.

The mutually confronting ends of the two chambers 3, 7 are separated from each other by a double-ended needle 12 held in position by a tubular guide member 13. The latter is divided into two by a central partition 13a through which the double-ended needle 12 passes. This tubular guide member 13 is able to slide, on the one hand into the open end of the tubular part 1, and on the other into the larger-diameter section 4b of the internal tubular support 4.

The two ends of the tubular guide member 13 of the double-ended needle 12 are each closed by a perforable plug 14 designed to ensure that the ends of the needle 12 do not prematurely perforate the films closing the mutually confronting ends of the vial 3 and of the cartridge 7, and to ensure that the needle is maintained in a sterile environment.

Two diametrically opposite elastic arms 15 are formed in the wall of the tubular part 2 in the vicinity of its open end in which the open end of the tubular part 1 is engaged. The internal surfaces of these arms 15 are shaped to fit the section 4b of the internal tubular support 4, as seen in FIG. 1b, thus preventing it from sliding relative to the tubular part 2. These arms also possess inclined surfaces 15a to allow the end of the tubular part 1 engaged in the tubular part 2 to push the arms out when the said end meets these inclined surfaces 15a after these two tubular parts 1, 2 have been slid into each other. This releases the internal tubular support 4 from the tubular part 2, as illustrated in FIG. 2b, and allows it to slide into this tubular part 2.

To connect the tubular parts 1, 2 to each other in such a way as to bring about a controlled sliding of these parts with respect to each other, the tubular part 1 possesses preferably two diametrically opposite side projections 16 engaged in two respective diametrically opposite guide grooves 17 formed in the wall of the tubular part 2. These guide grooves 17 are each made up of three parts, one part 17a designed to prevent the tubular parts 1, 2 from sliding relative to each other, one part 17b designed to determine the length of the sliding travel between these tubular parts and one part 17c that allows these tubular parts to slide in opposite directions and be separated from each other. As can be seen, when the two tubular parts 1, 2 are assembled initially in the position illustrated in FIG. 1a, the only way these tubular parts can be separated from each other is to move the side projection 16 along the section 17b of the guide groove 17, and then along the section 17c, which means that these parts can be separated from each other only after having first been pushed towards each other for a distance determined by the guide groove 17.

The end of the section 17b of the guide groove 17 may advantageously be slightly constricted, so that in order to reach the end of this section 17b, the side projection 16 has to slightly deform the portion of the wall of the tubular part 2 situated between the sections 17b and 17c of this groove 17. This slight deformation must not of course exceed the elastic limit of the material of which the tubular part 2 is made, so that after the side projection 16 has passed this constriction, the deformed section of the tubular part 2 can return to its initial shape, thereby preventing the side projection 16 from getting back into the section 17b of the groove 17.

FIGS. 1 to 3 illustrate the various stages in this sliding movement of the tubular parts 1, 2 inside each other. FIGS. 1a, 1b show the device for preparing a medicinal liquid in the rest position, in which the side projections 16 are in engagement with the axial locking sections 17a of the respective guide grooves 17. It is in this position that the device is supplied to users. The first step in transferring a defined volume of liquid from the vial 3 to the cartridge 7 is to slightly rotate the tubular parts 1, 2 relative to each other to disengage the side projections 16 from the sections 17a of the respective guide grooves 17. Pressure is then applied to the two tubular parts 1, 2 to slide them relative to each other until the side projections 16 reach the ends of the sections 17b of the guide grooves 17 and of the respective adjacent parts 17c.

The sliding of the two tubular parts 1, 2, corresponding to the projections 16 passing along the parts 17b of the grooves 17, enables two separate functions to be carried out, one function by the movement of the tubular parts 1, 2, corresponding to the transition from the position of FIGS. 1a and 1b to that of FIGS. 2a and 2b. As can be seen, during this first section of movement, the two neighbouring ends of the vials 3 on the one hand and the cartridge 7 on the other approach each other to the point of minimum separation in such a way that the two plugs 14 are pushed up against the partition 13a of the tubular guide member 13. During this movement the two ends of the needle 12 pass through the respective plugs 14 and through the films closing the respective ends of the vials 3 and of the cartridge 7, as illustrated in FIGS. 2a, 2b.

Figure 3A:
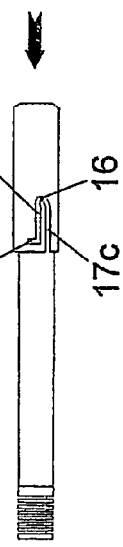
FIG. 3a is a side view similar to FIG. 2a, showing the device at the end of the liquid transfer process.

At the conclusion of this first section of this relative movement between the tubular parts 12, the forward end of the tubular part 1 meets the inclined surfaces 15a of the arms 15 and pushes them out as illustrated in FIG. 2b, releasing the internal tubular support 4, so allowing the tubular part 2 to slide relative to the internal tubular support 4 and relative to the tubular part 1, in such a way that it moves from the position illustrated in FIGS. 2a, 2b to that illustrated in FIGS. 3a, 3b. During this second section of the relative movement of the tubular parts, the cylindrical pusher 2a projecting from the bottom of the tubular part 2 pushes the plunger 6 of the liquid vial 3 towards the cartridge 7, transferring a defined volume of liquid into the latter. Because of the guide grooves 17 with which the side projections 16 of the tubular part 1 are in engagement, the length of the travel of the pusher 6, and consequently the volume of liquid transferred from the vial 3 to the cartridge 7, are constant and completely independent of the pressure exerted, of the reading of a graduation, or of a handling error.

Specifically, in order to be able to use the medicinal liquid contained in the cartridge 7, the two tubular parts must necessarily be separated from each other. However, in order to be able to separate them the side projections 16 must necessarily follow the guide grooves 17 from their starting point 17a to the outlet of the section 17c, which means that the sliding of the tubular parts relative to each other is precisely controlled by the guide grooves 17 and that as a consequence the movement of the plunger 6 is also precisely controlled.

In a preferred embodiment of the invention, the tubular part 1 is formed by the body of an injection syringe that has a pusher 18 to move the plunger 11 for injecting a dose of medicinal liquid prepared in accordance with the preparation process described earlier.

Figure 4:
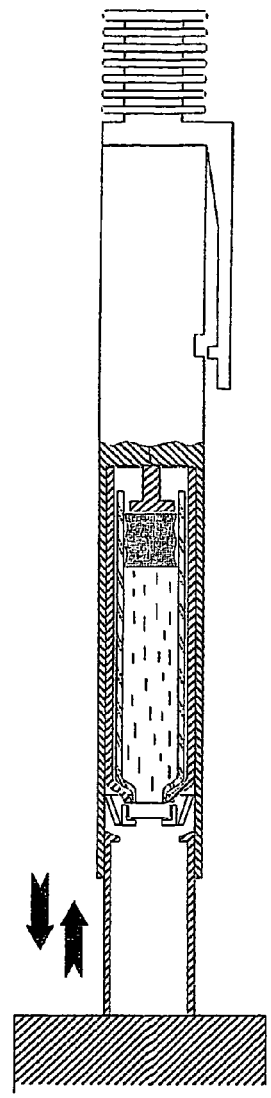
FIG. 4 is a view of one part of the device after its separation from the other part, once the medicinal liquid has been prepared.

For this purpose the internal tubular support 8 which holds the cartridge of liquid 7 in position in the tubular body 1 of the syringe reserves a space between the plunger 11 closing off the end of the cartridge 7 and the pusher 18. This space corresponds to the backward movement which the plunger 11 will have to undergo when the liquid is transferred from the vial 3 to the cartridge 7, so that following transfer of this liquid and separation of the tubular part 2 from the body 1 of the injection syringe, the syringe is ready to use after removal of the lock sleeve, as illustrated in FIG. 4.

The invention claimed is:

1. A device for preparing a medicinal liquid by combining a first liquid substance contained in a first variable-volume chamber and a second substance contained in a second chamber, the device, comprising:
   a first and a second tubular bodies each open at one end and closed at the other end,
   the respective open ends of the first and second tubular bodies being conformed to be engaged one into the other for a sliding movement,
   a first and a second internal tubular supports held in position respectively with respect to the first and second tubular bodies, for holding respectively in position the first variable-volume chamber and the second chamber,
   a double-ended needle for allowing these chambers to communicated with each other, and
   a pusher for engaging means for varying the volume of the first variable-volume chamber, device wherein
   the first internal tubular support has a smaller-diameter rear section for holding the first chamber and a larger-diameter forward section corresponding to the inside diameter of the first tubular body,
   the double-ended needle is held in position between the forward confronting ends of the first and second chambers by a central partition of a tubular guide member through which the double-ended needle passes, said tubular guide member being in slide engagement on the one hand into the open end of the second tubular body, and on the other hand into a larger-diameter forward section of the first internal tubular support,
   the end of the larger-diameter forward section of the first internal tubular support forming a stop for limiting the sliding movement of internal tubular supports one with respect to the other to a first section of sliding movement corresponding to passage of the respective ends of the double-ended needle into the first and second chambers,
   the said pusher projecting inside from the closed end of the first tubular body,
   the wall of the first tubular body comprising elastic arms the internal surfaces of which are shaped to fit the first internal tubular support for connecting the first tubular body and the first internal tubular support and for preventing the first internal tubular support from sliding relative to the first tubular body,
   inclined surfaces formed inside said elastic arms to be engaged by the end of the second tubular body at the end of the first section of the sliding movement, for releasing the first internal tubular support from the first tubular body allowing a second section of the said sliding movement of the first tubular body with respect to the first internal tubular support, during which the pusher of the first tubular body pushes the means for varying the volume of the first variable-volume chamber for transferring a defined volume of liquid from the first chamber to the second chamber.

2. The device according to claim 1, in which the two ends of the tubular guide member in which the double-ended needle is held in position are each closed by a performable plug to ensure that the needle is maintained in a sterile environment between the said chambers.

3. The device according to claim 1, in which all the components of which it is composed and the first variable-volume chamber and the second chamber are preassembled.

4. The device according to claim 1, comprising:
   a first stop for limiting a sliding of the tubular bodies into each other; and
   a second stop for limiting a penetration of the double-ended needle into the first and second chambers to a length less than the sliding of the tubular bodies into each other.

5. The device according to claim 4, wherein the first tubular body containing the second chamber consists of a syringe for injecting the medicinal liquid.

6. The device according to claim 4, wherein the first stop for limiting the sliding of the tubular bodies into each other comprises at least one guide path, integral with one of the tubular bodies, and at least one guided part integral with the other of the tubular bodies in engagement with the at least one guide path, the guide path comprising: an initial section in which the guided part is locked axially, corresponding to an axial position of greatest distance between the tubular bodies from each other, followed by a section to allow axial separation of the tubular bodies from each other.

7. The device according to claim 6, wherein the first tubular body containing the second chamber consists of a syringe for injecting the medicinal liquid.

8. The device according to claim 6, wherein an elastic means are provided between an end of a second section of the at least one guide path and a beginning of a third section of the at least one guide path, to prevent the guided part from returning, in engagement with the at least one guide path, into the second section of the at least one guide path after having reached an end of the second section of the at least one guide path, corresponding to a limit of mutual approach of the tubular bodies.

9. The device according to claim 8, wherein the first tubular body containing the second chamber consists of a syringe for injecting the medicinal liquid.

10. The device according to claim 4, wherein each of the sliding tubular bodies comprises at least two ends, a first end of each of the sliding tubular bodies possesses an elastic abutment to divide the sliding between the said tubular bodies into two sections, a first section coinciding with a penetration of the two ends of the double-ended needle into the respective chambers, and a second section occurring after the elastic abutment has been pushed out, coinciding with the reduction in volume of the first chamber, a second end of each of the tubular bodies being shaped to push the elastic abutment out to allow the tubular bodies to carry out the second section of their sliding.

11. The device according to claim 10, wherein the first tubular body containing the second chamber consists of a syringe for injecting the medicinal liquid.

12. The device according to claim 10, wherein the first stop for limiting the sliding of the tubular bodies into each other comprises at least one guide path, integral with one of the tubular bodies, and at least one guided part integral with the other of the tubular bodies in engagement with the at least one guide path comprising: an initial section in which the at least one guided part is locked axially, corresponding to an axial position of greatest distance between the tubular bodies from each other, followed by a section to allow axial separation of the tubular bodies from each other.

13. The device according to claim 12, wherein the first tubular body containing the second chamber consists of a syringe for injecting the medicinal liquid.

14. The device according to claim 1, wherein each of the sliding tubular bodies comprises at least two ends, a first end of each of the sliding tubular bodies possesses an elastic abutment to divide a sliding between the tubular bodies into two sections, a first section coinciding with a penetration of the two ends of the double-ended needle into the respective chambers, and a second section occurring after the elastic abutment has been pushed out, coinciding with the reduction in volume of the first chamber, a second end of each of the tubular bodies being shaped to push the elastic abutment out to allow the tubular bodies to carry out the second section of their sliding.

15. The device according to claim 14, wherein the first tubular body containing the second chamber consists of a syringe for injecting the medicinal liquid.

16. The device according to claim 14, wherein the elastic abutments, integral with one of the ends of each of the tubular bodies, is in engagement with the second stop for limiting the penetration of the said double-ended needle into the chambers, in such a way that the second stop is released from the elastic abutment when the elastic abutment is pushed out.

17. The device according to claim 16, wherein the first tubular body containing the second chamber consists of a syringe for injecting the medicinal liquid.

18. The device according to claim 14, wherein the first stop for limiting the sliding of the tubular bodies into each other comprises at least one guide path, integral with one of the tubular bodies, and at least one guided part integral with the other of the tubular bodies in engagement with the guide path, the guide path comprising: an initial section in which the at least one guided part is locked axially, corresponding to an axial position of greatest distance between the tubular bodies from each other, followed by a section to allow axial separation of the tubular bodies from each other.

19. The device according to claim 18, wherein the first tubular body containing the second chamber consists of a syringe for injecting the medicinal liquid.

20. The device according to claim 1, wherein the first tubular body containing the second chamber consists of a syringe for injecting the medicinal liquid.

21. The device according to claim 20, wherein the rear end of the second chamber is closed by a plunger, the second chamber being held in position by a tubular support in the first tubular body, reserving a space between said plunger and a member, integral with the syringe for operating the plunger corresponding to a distance the plunger of the second chamber must travel following the transfer of a predetermined volume of liquid from the first chamber to the second chamber.

* * * * *